(12) United States Patent
Khalfin et al.

(10) Patent No.: US 6,400,139 B1
(45) Date of Patent: Jun. 4, 2002

(54) METHODS AND APPARATUS FOR ELECTROMAGNETIC POSITION AND ORIENTATION TRACKING WITH DISTORTION COMPENSATION

(75) Inventors: Igor Khalfin, South Burlington; Herbert R. Jones, Jr., Williston, both of VT (US)

(73) Assignee: Polhemus Inc., Colchester, VT (US)

( * ) Notice: Subject to any disclaimer, the term of this patent is extended or adjusted under 35 U.S.C. 154(b) by 0 days.

(21) Appl. No.: 09/430,978

(22) Filed: Nov. 1, 1999

(51) Int. Cl.$^7$ .................................................. G01B 7/14
(52) U.S. Cl. ............................ 324/207.17; 324/207.12; 342/463
(58) Field of Search ................. 324/207.17, 207.12, 324/207.14, 207.15, 207.16, 207.26; 342/463, 448, 386; 340/979, 686.1; 701/207; 600/424; 128/899; 702/150

(56) References Cited

U.S. PATENT DOCUMENTS

| | | | |
|---|---|---|---|
| 4,287,809 A | 9/1981 | Egli et al. ........................ 89/41 |
| 4,314,251 A | 2/1982 | Raab ............................ 343/112 |
| 4,394,931 A | 7/1983 | Cotgreave et al. ........... 220/453 |
| 4,737,794 A | 4/1988 | Jones ........................... 342/448 |
| 5,453,686 A | 9/1995 | Anderson ............... 324/207.17 |
| 5,645,077 A | 7/1997 | Foxlin .......................... 128/774 |
| 5,752,513 A | 5/1998 | Acker et al. .............. 128/653.1 |
| 5,831,260 A | 11/1998 | Hansen ....................... 250/221 |

FOREIGN PATENT DOCUMENTS

EP          0747662 A1     6/1996

*Primary Examiner*—Jay Patidar
(74) *Attorney, Agent, or Firm*—Gifford, Krass, Groh, Sprinkle, Anderson & Citowski, PC

(57) ABSTRACT

Methods and apparatus for position/orientation tracking within a bounded volume employ at least one stationary sensor, called a "witness sensor," having a fixed position and orientation near or within the volume to account for electromagnetic distortion. One or more probe sensors are placed on an object to be tracked within the volume, and the output of each witness sensor is used to compute the parameters of a non-real effective electromagnetic source. The parameters of the effective source are used as inputs to the computation of position and orientation as measured by each probe sensor, as if the object were in the non-distorted electromagnetic field produced by the effective source or sources. In addition to trackers for helmet-mounted displays in aircraft, tank, and armored-vehicle applications, the invention finds utility in any electromagnetic tracking system which might be subject to electromagnetic distortion or interference. Such application areas include electromagnetic motion capture systems, and medical systems and instruments, among others.

28 Claims, 6 Drawing Sheets

METHODS AND APPARATUS FOR ELECTROMAGNETIC POSITION AND ORIENTATION TRACKING WITH DISTORTION COMPENSATION

FIELD OF THE INVENTION

This invention relates generally to position and orientation tracking and, in particular, to methods and apparatus for accurate position, orientation and motion-tracking within a bounded volume in the presence of electromagnetic distortion.

BACKGROUND OF THE INVENTION

Existing electromagnetic tracking systems, as well as inertial and combined inertial/optical and optical/magnetic tracers, are sensitive to various kinds of distortion. With respect to electromagnetic trackers, such distortion may arise from eddy currents in metal objects or from ferromagnetic materials, whereas, in the case of inertial trackers, drift or vibration might be the cause.

In inertial tracking systems, for example, as described in U.S. Pat. No. 5,645,077, requires an additional sensor, or set of sensors, to compensate for drift and movement of a vehicle or aircraft reference frame. Even with these additional sensors, such systems exhibit sensitivity to vibration, temperature instability requiring additional compensation. Inertial tracking systems also experience drift over time periods on the order of minutes to hours.

Combination systems, that is, systems which combine optical and magnetic sensing, are designed to compensate for distortion by comparison of the data from two different types of sensors. One such system is described in U.S. Pat. No. 5,831,260 to Hansen. The use of combination systems with an optical tracking module (e. g., inertial/optical or magnetic/optical) is restricted to applications where interference associated with night-vision devices is significant, or when parasitic illumination or optical noise is present.

In an electromagnetic tracking environment, distortion may arise from eddy currents induced in nearby metal objects or from ferromagnetic materials. Eddy currents, in turn, generate fields that interfere with the field from the source(s) used for tracking purposes. To compensate for distortion of this kind, one solution involves the use of mapping. With mapping, the electromagnetic field in a volume of interest, as distorted by metal objects, is defined in advance and used to solve for position and orientation. Commonly assigned U.S. patent application Ser. No. 09/215,052, the entire contents of which are incorporated herein by reference, discloses, as part of a preferred embodiment, the use of Green's functions in conjunction with such field mapping.

The need remains, therefore, for a simple but effective approach to reducing the effects of distortion in an electromagnetic tracking system. Ideally, such a solution would be useful in a variety of applications, including military, motion capture and medical instrumentation.

SUMMARY OF THE INVENTION

The subject invention is directed to distortion compensation in electromagnetic position and orientation tracking configurations. Among the advantages over previous approaches, the invention eliminates the need for mapping in advance of actual measurements and, permits real-time adjustment in the event that new field distorters arise. This may be significant in such an environment as aircraft cockpit or tracing of medical/surgery instruments.

The invention is specifically applicable to position/orientation tracking systems of the type wherein the components of an AC electromagnetic field are sensed within a bounded volume. As in previous designs, one or more probe sensors are placed on an object being tracked within the volume, each measuring the magnetic induction vector components of the field generated by the source to determine the position, orientation and movement of the object within the volume. However, to compensate for electromagnetic distortion, the invention employs it least one stationary sensor, termed a witness sensor, in addition to the probe sensor(s) disposed on the object. Each witness sensor is supported at a known, fixed position and orientation relative to the reference frame of interest, at a point near or within the volume of interest, and close to the sensors on the object being tracked.

The outputs of each probe sensor, and each witness sensor, are delivered to a processing unit operative to compute the position and orientation of the object in the presence of electromagnetic field distorters. The processor uses data from each witness sensor to compute parameters, such as the position, orientation, and strength, of an effective electromagnetic source or sources. The effective source(s), which may be treated for the sake of simplicity as a point source (wherein the size of the source is negligible in the scale of measured distances) or a dipole (wherein the field is described by the dipole equation), would produce the same field as a superposition of the real source plus field of distortion in the proximity of witness sensors. Note that in the case of a non-distorted quiet environment, the single effective source will coincide with, and will be identical to, the actual real source. This allows the computed parameters of the effective source(s) to be used as inputs to the computation of position and orientation as measured by each probe sensor, as if the object is in the non-distorted electromagnetic field produced by the effective source(s).

An electromagnetic position/orientation tracking system according to the invention therefore preferably includes a real source of an AC electromagnetic field driven by the system; at least one witness sensor measuring electromagnetic induction vector components at a known spatial point with respect to the real source of an AC electromagnetic field; one or more probe sensors measuring electromagnetic induction vector components from the perspective of the object; and a control/processing unit providing the requisite computations. In addition to trackers for helmet-mounted displays in aircraft, tank, and armored-vehicle applications, the invention finds utility in any electromagnetic tracking system which might be subject to electromagnetic distortion or interference. Such application areas include electromagnetic motion capture systems, and medical systems and instruments, among others.

DETAILED DESCRIPTION OF THE INVENTION

Figure 1:
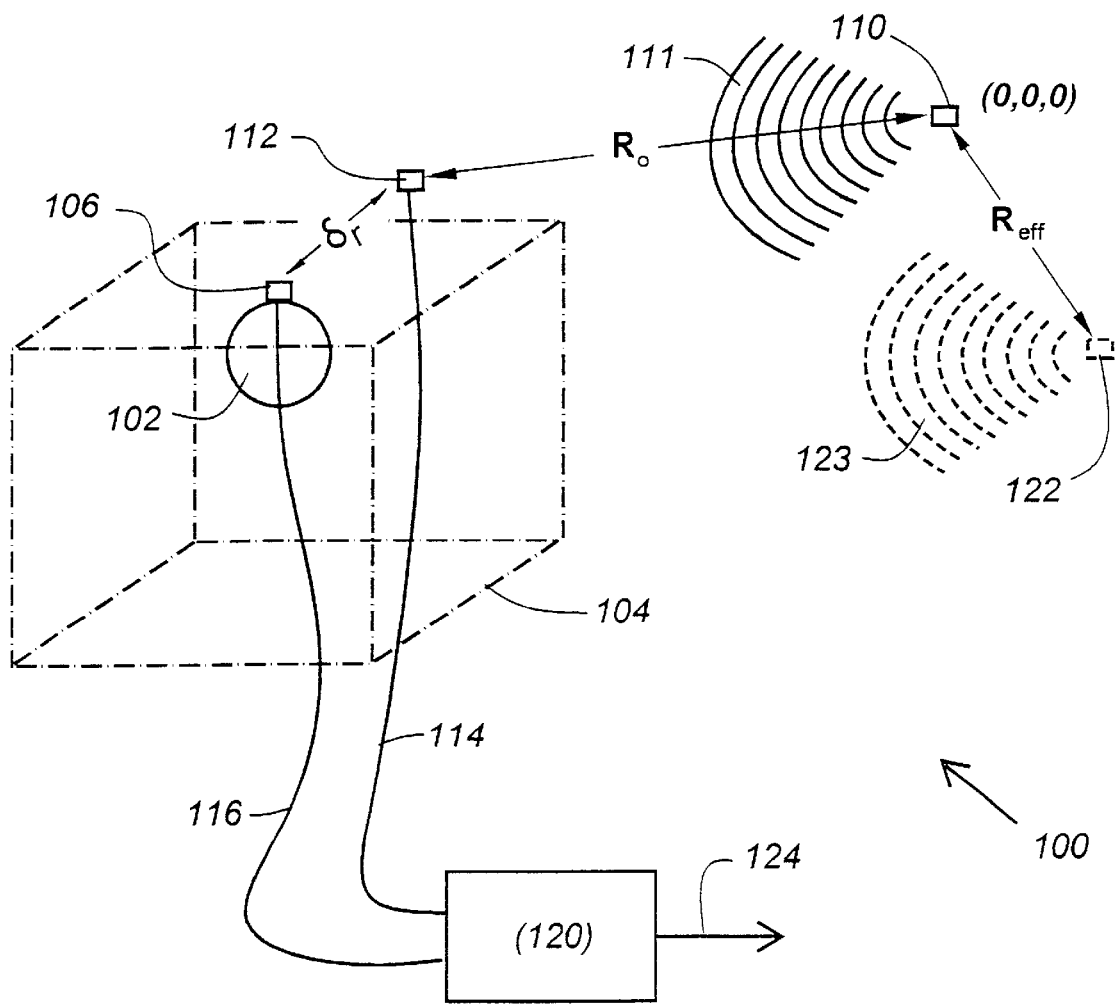
FIG. 1 is a drawing which illustrates a preferred embodiment of the invention.

FIG. 1 illustrates, generally at 100, apparatus associated with a preferred embodiment of the invention. An object 102 is to be tracked within a volume of interest 104, wherein electromagnetic distortion may be present. One or more probe sensors 106 are supported on the object to measure magnetic induction-vector components of an AC electromagnetic field 111 generated by a real, physical source 110. A stationary "witness" sensor 112 (or a set of sensors) having a known position and orientation is disposed at a known distance $R_0$ (or distances) from the source 110.

Figure 4:
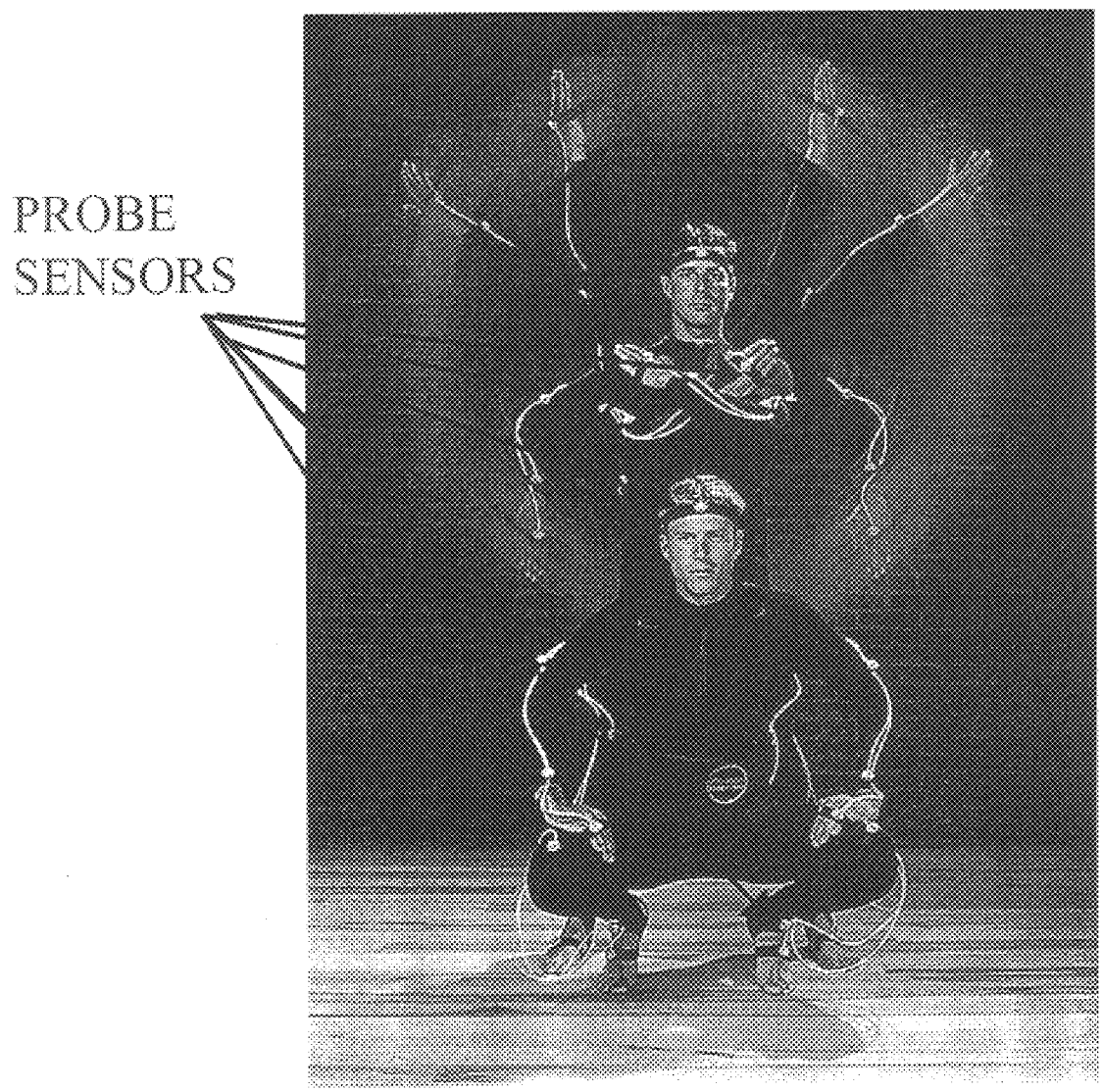
FIG. 4 shows the use of multiple probe sensors on a human body for sport medicine and motion capture/animation applications.
Figure 5:
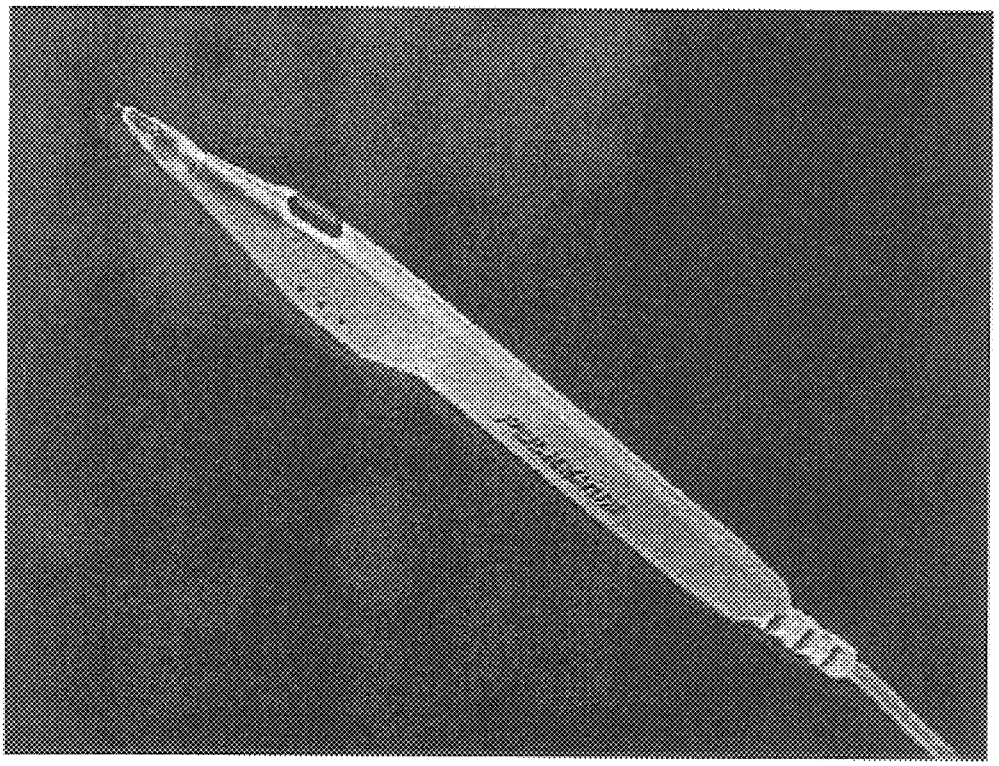
FIG. 5 shows a probe sensor embedded into a stylus for medical/graphics applications.

The witness and probe sensors 112 and 106 are interconnected through paths 114 and 116 to a processor unit 120, which outputs the position and orientation of the object 102 within the volume 106. Although multiple, single-axis sensors may be used for the probe or witness sensors, the invention preferably uses multi-axis sensors measuring three components of the induction vector. Magnetic field data from each witness sensor are used by the processor unit 120 to calculate the position, strength and orientation of an "effective" source (or sources) 122 located at a distance $R_{eff}$ from witness sensor. The effective source 122 is not a real source but a model source which would produce the electromagnetic field, in the vicinity of the witness sensor equivalent to the superposition of the fields from the actual source and from the electromagnetic distortion due to the eddy currents which may be present. Depending on the required accuracy and processing time, there are at least two options to treat this effective source: the first one, is to consider a single effective source that will create the same field as the actual source plus distortion field; the second option is to consider single or multiple effective sources in addition to the actual source, thus considering the field as a superposition of the real source and the effective source(s) modeling distortion. The second option is more accurate but requires more intensive real-time computations. The result is used to determine the position and orientation of each probe sensor 106 and, hence, the object 102, as measured in the non-distorted field 123 produced by the effective source 122 (or superposition of the field of the real source 110 and effective source(s) 122 ). The distortion is therefore automatically taken into account. Probe sensors may be used to determine the motion of body parts (FIG. 4) or used on surgical or digitizing instruments (FIG. 5).

Figure 6:
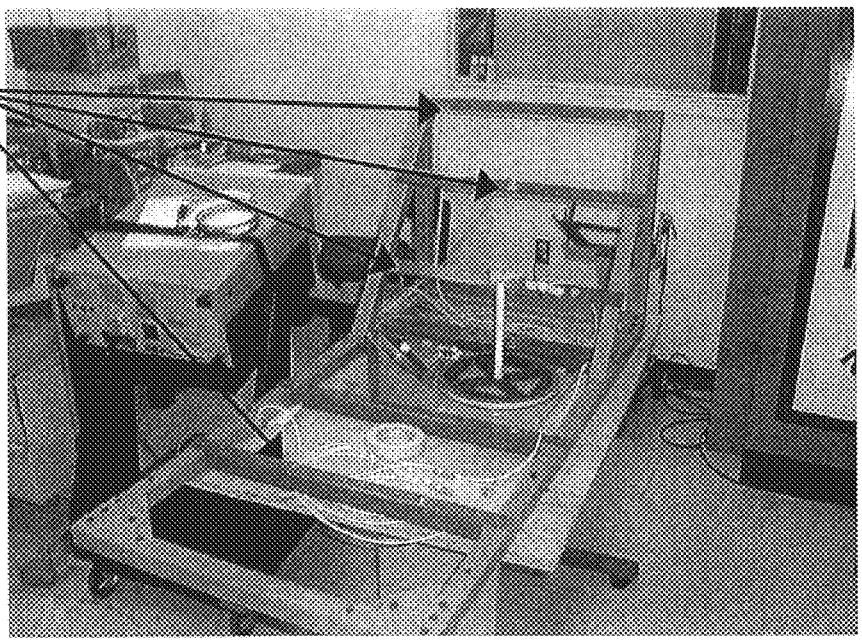
FIG. 6 shows an implementation according to the invention using multiple witness sensors on a rigid structure.

The inventive system does not require mapping and, in fact, the witness sensor data are self-calibrating. Although the volume depicted in FIG. 1 is a cube, the system works with any geometry. Although mapping approaches benefit from the use of regular geometric volumes, since this invention does riot require a priori mapping, arbitrary volumes shapes are readily accommodated. The witness sensor (s) need not be placed within the volume. One of the options is illustrated in FIG. 6. where the volume of interest is above a fixture incorporating multiple witness sensors. The only assumption underlying optimum results is that the witness sensor(s) and probe sensor(s) are close enough to one another.

Mathematically, the arrangement may be described as follows:

Let $B(R_0)$ be the magnetic induction vector measured by a witness sensor located at the point $R_0$ and a real source of the electromagnetic radiation located at the origin. This magnetic field may be described exactly by the equation:

$$B(R_0) = -\text{grad} \int_V G(r)\rho(r)d^3 r - \text{grad} \sum \int_{V_{dist}} G(R_0 + R_{dist})\rho(R_0 + R_{dist})d^3 R_{dist}$$

where G is the Green's function and is the density function.

The first term of the above equation describes the field created by the source at the point $R_0$. The second term describes the field of the spatially distributed distortion in the sub-volumes $V_{dist}$. Note that although the actual source is placed at (0,0,0) in this case, any suitable alternative location may be used through appropriate coordinate transformation. In the case of multiple witness sensors (e. g. N sensors) we will get a set of N similar equations with corresponding substitution of $R_{0i}$ instead of $R_0$, i=1.N.

The same field $B(R_0)$ may be described approximately as the field of some effective source (the first option, as described above) located around some point $R_{eff}$, as follows:

$$B(R_0) = -\text{grad} \int_{V_{eff}} G(R_0 + R_{eff} + r)\rho(R_0 + R_{eff} + r)d^3 r$$

second option, as described above, will yield the equation:

$$B(R_0) = -\text{grad} \int_V G(r)\rho(r)d^3 r - \text{grad} \sum \int_{V_{eff}} G(R_0 + R_{eff} + r)\rho(R_0 + R_{eff} + r)d^3 r$$

The solution of these equations with respect to $R_{eff}$ and □ may be found, for example, by the best-fit method or by the quasi-Newton method. It should be noted that the above equations employ the superposition principle (see references above). However, the integral over Veff may be split into few integrals over few effective volumes, e. g. Veff=Veff1+Veff2+ . . . ,in this case the solution of the above equations may be represented as a sum of few effective sources located at Reff1, Reff2, . . . , that means that superposition of the field from the actual source and distortion field will be represented by the superposition of few effective sources. The choice of the representation depends on practically required accuracy.

The solution to the above vector equation is the input to the next equation, which describes the electromagnetic field at the location of the probe sensor:

$$B(R_{eff} + R_0 + \delta r) = -\text{grad} \int_{V_{eff}} G(R_{eff} + \delta r + r)\rho(R_{eff} + r)d^3 r$$

The solution (vector) with respect to r, i.e., the position of the probe sensor, defines the output of the system.

The accuracy of the system is enhanced through placement of the witness sensor(s) in close proximity to the probe sensor(s). That is, accuracy is increased when:

$r<<R_0, R_{eff}$

Multiple witness sensors increase the accuracy of the solution with respect to $R_{eff}$ and, in turn, r In addition, the volume wherein sufficient accuracy is achievable increases.

Figure 2:
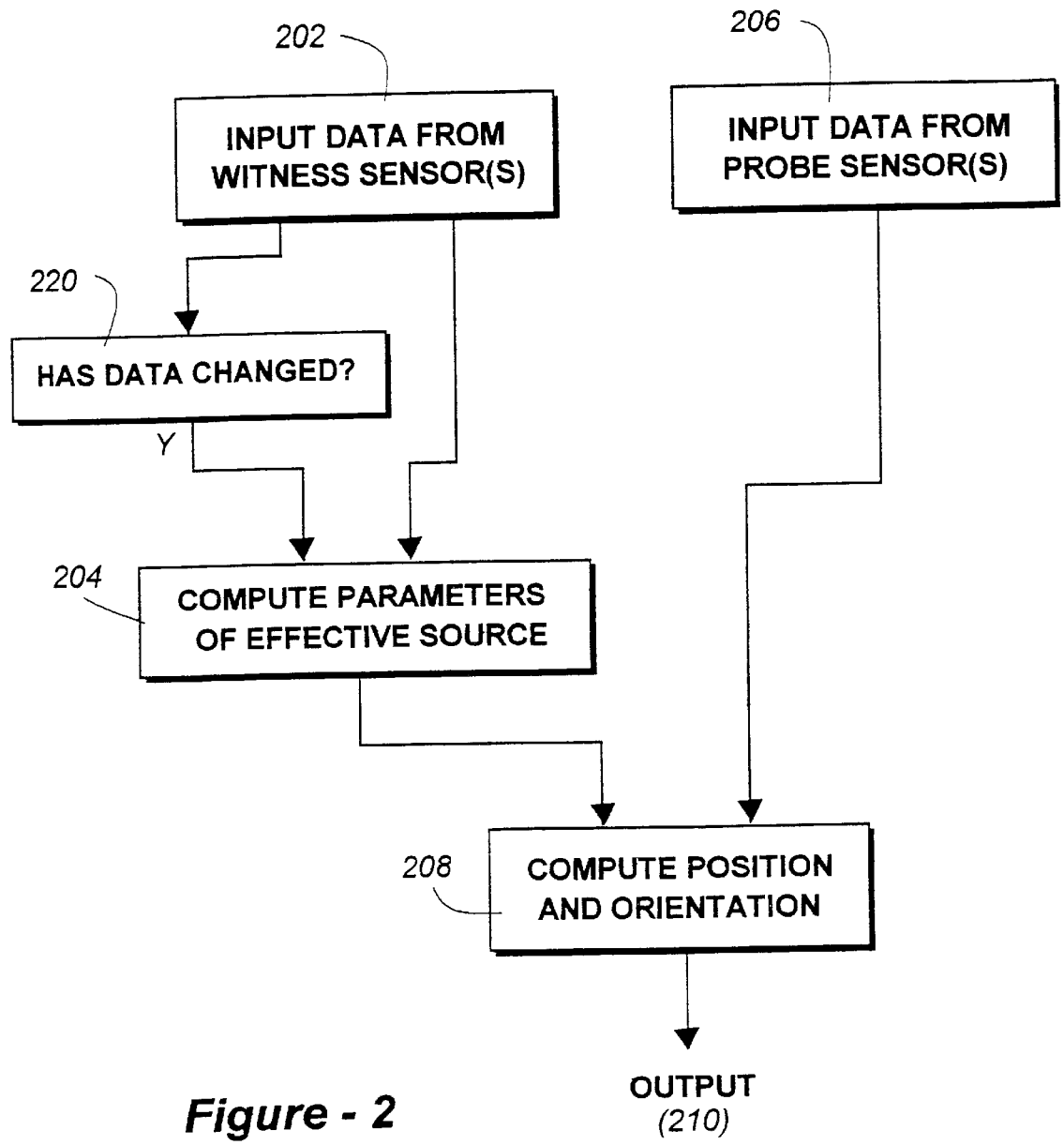
FIG. 2 is a flow diagram that illustrates the steps of a preferred method of carrying out the invention.

A flow diagram of the method is presented in FIG. 2. At step 202, input data from the witness sensor(s) are gathered. At block 204 the parameters of the effective source(s) are computed, that are position and magnetic properties of the effective source(s) measured in the reference frame of the actual source. If the data from the witness sensor(s) have changed, this is taken into account at step 220. At step 206, input data from the probe sensor(s) are gathered. At step 208, the position and orientation of the object is computed relative to the coordinates of the volume of interest using the inputs from the witness and probe sensors, and the output is delivered at 210. An advantage of the invention is that the solution for the effective source may be computed at regular intervals or real-time, allowing for essentially continuous noise compensation, since witness and probe sensors are preferably at the same approximate location, and therefore nearly equally affected by the external noise. (e.g., RF).

Figure 3:
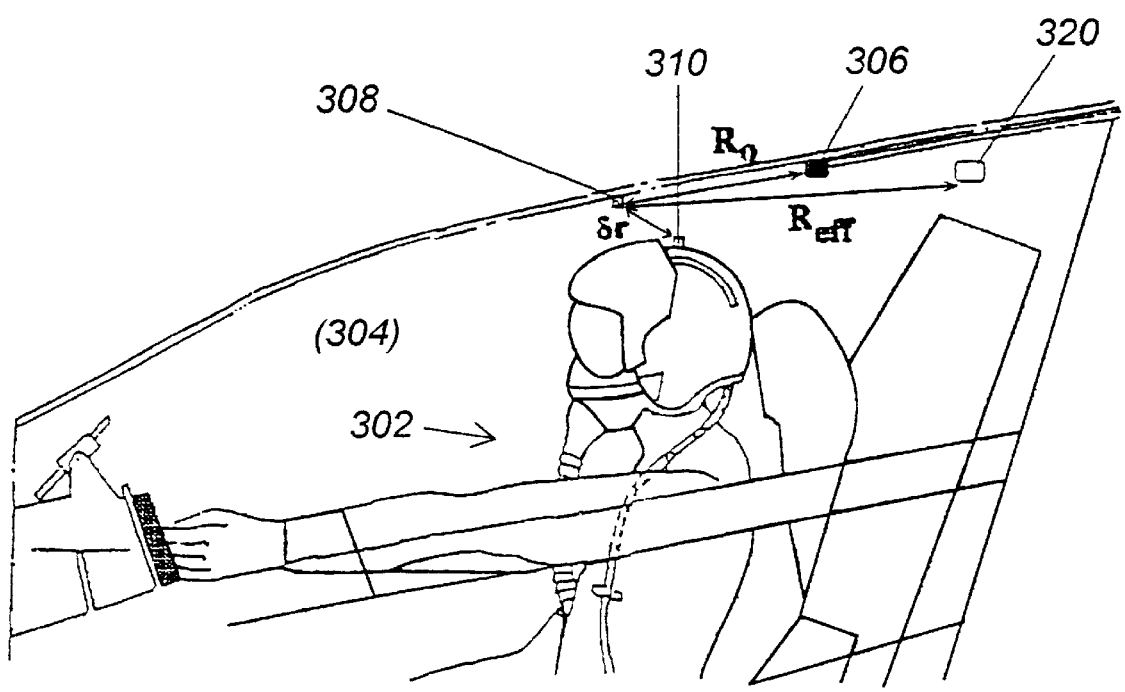
FIG. 3 is a drawing which depicts a specific application of the invention, namely, a helmet-mounted aircraft tracking configuration.

FIG. 3 is a drawing of an aircraft cockpit application of the invention. In this case a pilot 302 moves within a volume 304. A source 306 radiates an AC electromagnetic field within the volume, which is received by at least one witness sensor 308 and at least one probe sensor 310 mounted on the helmet of the operator 302. A processing unit (not shown) receives the inputs from the sensors, and computes the position and orientation of the object, in this case the helmet of the pilot, by applying the effective field generated by source 320 (or superposition of fields from 320 and 306) to the components of the field measured by the probe sensor 310.

In addition to trackers for helmet-mounted displays in aircraft, tank, and armored-vehicle applications, tracing of medical/surgery instruments the invention finds utility in any electromagnetic tracking system which might be subject to electromagnetic distortion or interference. As disclosed in co-pending U.S. patent application Ser. No. 09/215,052, such application areas include electromagnetic motion capture systems, and medical systems and instruments, among others. FIG. 4 shows the use of multiple probe sensors on a human body for sport medicine and motion capture/animation applications. FIG. 5 shows a probe sensor embedded into a stylus for medical/graphics applications. FIG. 6 shows an implementation according to the invention using multiple witness sensors on a rigid structure.

We claim:

1. Apparatus for determining the position and orientation of an object within a bounded volume of interest in the presence of electromagnetic distortion, the apparatus comprising:

a real source of an electromagnetic field having measurable magnetic induction-vector components;

one or more stationary witness sensors supported near or within the volume of interest, each witness sensor being operative to measure the induction-vector components using a fixed known position and orientation;

one or more probe sensors supported on the object for measuring the induction-vector components; and a processor in communication with each witness sensor and each probe sensor, the processor being operative to perform the following functions:

a) compute the characteristics of at least one effective electromagnetic source, the effective source being defined as a model source which would produce the field in the vicinity of each witness sensor similar, or identical, to the field generated by the real source, along with electromagnetic distortion present in the volume, b) receive the induction-vector components measured by each probe sensor, and c) compute the position and orientation of the object by applying the spatial and electromagnetic magnetic characteristics of the effective source to the induction-vector components measured by each probe sensor.

2. The apparatus of claim 1, wherein:

the object moves within the volume; and at least functions b) and c) performed by the processor are repeated at regular intervals to track the motion of the object.

3. The apparatus of claim 1, wherein the computed characteristics of the effective source include the strength, position and orientation of the effective source.

4. The apparatus of claim 1, wherein the bounded volume includes at least a portion of a vehicle interior, and wherein each probe sensor is supported relative to an operator of the vehicle.

5. The apparatus of claim 4, wherein vehicle interior forms part of an aircraft cockpit, and wherein each probe sensor is mounted on a helmet worn by the operator.

6. The apparatus of claim 1, wherein at least one probe sensor is positioned on a medical instrument.

7. The apparatus of claim 1, wherein at least one probe sensor is positioned on a person's body.

8. The apparatus of claim 1, including a plurality of witness sensors, and wherein the characteristics of the effective source are determined by the best-fit approximation.

9. The apparatus of claim 1, including a plurality of witness sensors, and wherein the characteristics of the effective source are determined by an error minimization or optimization procedure.

10. The apparatus of claim 1, wherein the effective source is treated as a point source.

11. The apparatus of claim 1, wherein the effective source is treated as a dipole source.

12. The apparatus of claim 1, wherein each witness sensor and each probe sensor measures orthogonal components of the magnetic induction vector given a known reference frame of witness sensor(s).

13. A method of determining the position and orientation of an object within a bounded volume in the presence of electromagnetic distortion, comprising the steps of:

a) generating an electromagnetic field having magnetic induction-vector components from a stationary source;

b) measuring the components of the electromagnetic field at one or more stationary points near or within the volume;

c) measuring the components of the electromagnetic field at one or more points relative to the object;

d) computing the characteristics of an effective electromagnetic field, which would be produced by the stationary source in the vicinity of a given witness sensor along with electromagnetic distortion present in the bounded volume;

e) receiving the induction-vector components measured relative to the object; and f) computing the position and orientation of the object by applying the characteristics of the effective field to the induction-vector components.

14. The method of claim 13, wherein:

the object moves within the volume; and at least steps e) and f) are repeated at regular intervals to track the motion of the object.

15. The method of claim 13, wherein the step of computing the characteristics of the effective electromagnetic field include computing the strength, position and orientation of the effective field.

16. The method of claim 13, wherein the object is positioned within a vehicle interior.

17. The method of claim 13, wherein the object is supported on the body of an individual.

18. The method of claim 13, wherein the step of computing the characteristics of the effective electromagnetic field includes the step of performing a best-fit approximation.

19. The method of claim 13, wherein the step of computing the characteristics of the effective electromagnetic field includes the step of performing an error minimization or optimization procedure.

20. The method of claim 13, further including the step of treating the effective source as a point source.

21. The method of claim 13, further including the step of treating the effective source as a dipole source.

22. The method of claim 13, wherein components of the induction vector are measured at each stationary point.

23. The method of claim 13, wherein components of the induction vector are measured at each point relative to the object.

24. In a position/orientation tracking system of the type wherein AC electromagnetic radiation is received by a probe sensor disposed on an object being tracked in the presence of electromagnetic distortion, the improvement comprising:
   at least one witness sensor having a known fixed position and orientation within the field relative to the source of the electromagnetic distortion; and
   processor means in communication with the witness sensor for:
   a) computing a non-distorted model field proximate to the witness sensor, and
   b) computing the position and orientation of the object with probe sensor attached to the object as if the object were located within the non-distorted model field.

25. The improvement of claim 24, wherein the witness sensor is in close proximity to the object.

26. The improvement of claim 24, further including a plurality of spaced-apart witness sensors.

27. The improvement of claim 24, further including a plurality of sensors on the object being tracked.

28. The improvement of claim 24, wherein the object is supported on a person's body.

* * * * *

UNITED STATES PATENT AND TRADEMARK OFFICE
CERTIFICATE OF CORRECTION

PATENT NO.    : 6,400,139 B1
DATED         : June 4, 2002
INVENTOR(S)   : Igor Khalfin It is certified that error appears in the above-identified patent and that said Letters Patent is hereby corrected as shown below:

Column 2,
Line 10, replace "it least" with -- at least --.

Column 3,
Line 55, replace "riot" with -- not --.

Column 8,
Line 19, replace "of sensors" with -- of probe sensors --.

Signed and Sealed this

Thirty-first Day of December, 2002

JAMES E. ROGAN
*Director of the United States Patent and Trademark Office*